United States Patent [19]
Boeren et al.

[11] Patent Number: 4,652,280
[45] Date of Patent: Mar. 24, 1987

[54] ADSORPTION MATERIAL FOR OLEFINS, GAS CHROMATOGRAPHY COLUMN, METHOD OF SELECTIVELY REMOVING OLEFINS FROM A MIXTURE OF HYDROCARBONS

[75] Inventors: Edward G. Boeren, Utrecht; Richard B. van Henegouwen, The Hague, both of Netherlands

[73] Assignee: Packard Instrument B.V., Delft, Netherlands

[21] Appl. No.: 741,169

[22] Filed: Jun. 4, 1985

[30] Foreign Application Priority Data

Jun. 6, 1984 [NL] Netherlands ......................... 8401805

[51] Int. Cl.$^4$ ............................................ B01D 15/08
[52] U.S. Cl. .......................................... 55/67; 55/197; 55/386
[58] Field of Search ........................... 55/67, 197, 386; 210/656, 690

[56] References Cited

U.S. PATENT DOCUMENTS

| | | | |
|---|---|---|---|
| 2,865,970 | 12/1958 | Thomas | 260/676 |
| 3,219,717 | 11/1965 | Niles | 260/666 |
| 3,357,158 | 12/1967 | Hollis | 55/67 |
| 3,790,475 | 2/1974 | Eaton | 55/386 X |
| 3,940,972 | 3/1976 | Norell et al. | 55/67 X |
| 3,969,344 | 7/1976 | Ackermann et al. | 210/690 X |
| 4,043,905 | 8/1977 | Novotny et al. | 55/386 X |
| 4,140,653 | 2/1979 | Imura et al. | 55/386 X |

OTHER PUBLICATIONS

Arustamova et al., "Surface-Layer Sorbents for Group Analysis of Aromatic Hydrocarbons in Petroleum Distillates", J. of Chromatography, 140 (1977) 319–321.

Ury, "Automated Gas Chromatographic Analysis of Gasolines for Hydrocarbon Types", Anal. Chem. 1981, 53, 481–485.

Wasiak et al., "Investigation of Interaction of Olefin--Bonded Transition Metal Complexes by Gas Chromatography, Diphenylphosphine Complexes with $CoCl_2$ and $CoBr_2$", Chromatographia vol. 18, No. 4, Apr. 1984, pp. 205–210.

Hewlett Packard, "Hydrocarbon Type Analyzer for Naphthas and Gasolines", application note AN 228-24, 7 pages.

McTaggart et al., "Molecular Sieves for the Analysis of Petroleum", J. Anal. Chem. 290, 1–9 (1978).

Berezkin, "Subtraction Method and Its Application in Gas Chromatograhy", Anal. Chem. 296, 1–17 (1979).

Robinson et al., "Rapid Hydrocarbon-Type Analysis of Gasoline by Dual Column Gas Chromatography," Anal. Chem. vol. 43, No. 4, Apr. 1971, pp. 591–594.

Primary Examiner—Robert Spitzer
Attorney, Agent, or Firm—Weingarten, Schurgin, Gagnebin & Hayes

[57] ABSTRACT

This invention relates to an adsorption material for olefins, a gas chromatography column and a method for removing olefins from a mixture with saturated hydrocarbons by gas chromatography. The adsorption material according to the invention is a thermostable, macroporous resin having strongly acid ion exchange groups to which silver ions are linked. The resin has an average pore diameter of 10–100 nm, an internal surface area of 10–100 m$^2$/g and 5–15% cross-linking.

23 Claims, No Drawings

ADSORPTION MATERIAL FOR OLEFINS, GAS CHROMATOGRAPHY COLUMN, METHOD OF SELECTIVELY REMOVING OLEFINS FROM A MIXTURE OF HYDROCARBONS

This invention relates to an adsorption material for olefins, and also to a gas chromatography column filled with an adsorption material for olefins.

The invention further relates to a method of selectively removing olefins from a mixture of hydrocarbons containing olefins and saturated hydrocarbons, in which the mixture to be separated is passed in the gaseous state through a gas chromatography column.

For preparative and especially analytical purposes, there is a need for a method which makes it possible to separate the various types of compounds present in a mixture of hydrocarbons. This need exists, for example, with naphtha, i.e. a mixture of saturated hydrocarbons, aromatic hydrocarbons and olefins, obtained from crude oil, for example, by distillation and cracking. In order to analyze such a mixture of hydrocarbons, it is generally first subjected to a column chromatographic treatment, in which the aromatic hydrocarbons are selectively removed from the mixture. The aromatics sorbed by the column packing can subsequently, if desired, be separated and analyzed according to the number of carbon atoms.

The mixture of saturated hydrocarbons and olefins that remains after the removal of the aromatics is subjected to a column chromatographic treatment, in which the olefins are selectively removed from the mixture. Both the olefins and the saturated hydrocarbons can subsequently be subjected to further separation methods to make a detailed analysis possible. Thus the saturated hydrocarbons are commonly separated into isoparaffins, normal paraffins and naphthenes, followed by separation according to the number of carbon atoms. The olefins are commonly, after desorption and hydrogenation, separated into branched olefins, straight-chain olefins, and cyclic olefins, followed by carbon number separation.

However, there has not so far been an efficient method of removing the olefins from a mixture of olefins and saturated hydrocarbons by a selective and reversible adsorption of the olefins in a gas chromatography column.

Known in the art is the adsorption of olefins on mercury perchlorate on a solid carrier, such as Cromosorb P. See for example Huber et al, Hewlett Packard Application Note AN 228-24; McTaggart et al, Z. Anal. Chem. 290, 1-9 (1978); Berezkin, Z. Anal. Chem. 296, 1-17 (1979); and Robinson et al, Anal. Chem. 43, 591-594 (1971).

In this known method, however, the adsorption is irreversible; a quantitative determination of the olefin content is realized by the so-called subtraction technique, in which the difference in peak area between an injection without an olefin trap and an injection with an olefin trap is attributed to the olefins.

Shulz et al, Erdöl und Kohle-Erdgas-Petrochemie Vol. 27, no. 7 (1974), pp 345-352 have described a reversible adsorption of olefins on silver nitrate on Sterchamol.

Arustanova et al, J Chrom.140, 319-321 (1977) have described a reversible adsorption of olefins on silicagel dust impregnated with sodium hydroxide on Celite-545, intended for a separation of aromatics and saturated hydrocarbons.

Ury, Anal. Chem. 53, 481-485 (1981) has described a reversible adsorption of olefins on copper (II) sulfate on silicagel.

These prior methods for reversible adsorption, that is to say, the temporary removal of olefins, all concern the use of certain inorganic salts on a limited number of solid supports and have in common that a selective reversible adsorption of olefins requires the presence of water vapour, which reinforces the ionic character of the salts.

A disadvantage of the requisite presence of water, however, materializes in the subsequent solid-state chromatography treatment with porous polymers in that the water affects retention times and results in non-reproducible quantitative results.

Wasiak et al, Chromatographia Volume 18, no. 4, (April 1984), pp 205-210 have proposed to remedy this problem by using as the sorption material complexes of diphenyl phosphine with $CoCl_2$ or $CoBr_2$, chemically linked to a silicon dioxide support (Porasil C).

This, however, has the drawback that no selective adsorption of olefins takes place.

U.S. Pat. No. 3,219,717 discloses a method of removing traces of olefins from saturated hydrocarbons, in which a liquid feed is passed through a column packed with an adsorption material for the olefins. This adsorption material consists of a thermostable resin having acid ion exchanging groups, such as carboxylic acid groups or sulfonic acid groups to which silver ions are linked. One example of such an adsorption material is a Dowex 50W-X8 resin (sulfonated styrene divinylbenzene copolymer) to which $Ag^+$ ions are linked. This microporous adsorption material is capable of adsorbing olefins at low temperatures (below 30° C. whereafter desorption is possible at temperatures of 40°-100° C.

Disadvantages of this known adsorption material are that it is unsuitable for gas chromatography and incapable of realizing a selective and reversible removal of a group of olefins having different numbers of carbon atoms from a gaseous complex mixture containing olefins and saturated hydrocarbons with different numbers of carbon atoms.

The present invention provides an adsorption material for olefins comprising a thermostable resin with strongly acidic ion exchange groups to which $Ag^+$ ions are linked, which avoids the above disadvantages and is characterized in that the resin is a macroporous resin with an average pore diameter of 10-100 nm, an internal surface area of 10-100 $m^2/g$, and 5-15% cross-linking.

It is definitely surprising that, unlike microporous resin, the use of a macroporous resin permits a selective and reversible removal of a group of olefins from complex mixtures, since macroporosity would expect to make for stronger retention of saturated hydrocarbons by Van der Waals adsorption and to have no effect on the retention of olefins which, in fact, is brought about by chemical bonding to the silver ions. Quite unexpectedly, however, a higher selectivity for olefins and reversibility have been found.

For that matter, Netherlands patent applications Nos. 74.16607 and 76.12632 describe an adsorption material for olefins which is a macroporous resin with strongly acidic ion exchange groups to which $Ag^+$ ions are linked. Although these publications prescribe a specific area of at least 1 $m^2/g$ and an average pore diameter of at least 1 nm, the only material exemplified, in fact, is the commercially available resin Amberlite XE-284 (sulfonic acid type) with an average pore diameter of no more than 4–5 nm and a specific area as high as 570–580 m$^2$/g. Moreover, in these publications, this adsorption material is only used in a process for separating unsaturated compounds from liquid hydrocarbon mixtures. Desorption, as described in Netherlands patent application No. 7416607, is realized by displacement in the liquid phase with a normally gaseous hydrocarbon at a temperature of 10°–40° C. and a pressure of 1–30 ato, and, according to Netherlands patent application No. 7612632, by displacement of a monocyclic aromatic hydrocarbon at a temperature of 50°–150° C. and at normal pressure.

The adsorption material according to the present invention, which is based on a macroporous resin with an average pore diameter of 10–100 nm, an internal surface area of 10–100 m$^2$/g and 5–15% cross-linking is not known from these publications anymore than its suitability and use for gas chromatographic separation of a complex mixture of hydrocarbons, with desorption being effected by increasing the temperature.

Preferably, according to the invention, the strongly acidic ion exchange groups are sulfonic acid groups.

Ion exchangers containing carboxylic groups as functional groups belong to the weakly acid type and have been found to be unsatisfactory.

As the carrier, a thermostable macroporous resin is used. Any resin satisfying this definition is suitable. Highly suitable are resins on the basis of polystyrene cross-linked with divinylbenzene. Large pores in the order of 10–100 nm, preferably 30–100 nm, and most preferably about 40 nm, are excellently suitable. Good results are obtained when the particles have sizes in the range of 0.037–0.84 mm, preferably 0.07–0.2 mm.

The resin preferably has a porosity of about 25%, an internal area of 10–100 m$^2$/g, most preferably about 25 m$^2$/g and 5–15%, most preferably about 8%, cross-linking.

It is believed that the selective adsorption of olefins can be attributed to the formation of a $\pi$-bonding between an olefin and a silver ion, which $\pi$-bond is composed of two interdependent components: a sigma-type interaction as a result of a transition of $\pi$-electrons from the occupied 2p bonding orbital of the C=C system into the vacant 5s orbital of the silver ion, and a $\pi$-type interaction resulting from a return of d electrons from occupied 4d orbitals of the C=C system. The strength of the bonding between the olefins which acts as a ligand and the resin treated in accordance with this invention is such that even at elevated temperatures the olefins are sufficiently trapped (retained) or retarded. The olefins can be released by thermal desorption, so that the adsorption material according to the invention can be used in gas chromatography systems without any problems.

It will be understood from the above explanation that the term "adsorption material" is used herein in a broad sense and is not intended to be construed as referring to mere physical adsorption. The material according to the invention could be designated more concretely by the term "chemisorption material".

The preparation of the adsorption material according to this invention presents no problems to those skilled in the art. The preparation of a macroporous resin, for example, of the polystyrene type, cross-linked with divinylbenzene, which resin carries sulfonic acid groups as functional groups, is known per se. By means of ion exchange chromatography, the proton of the sulfonic acid group can be replaced by an Ag$^+$ ion, After careful drying, the resin in the Ag$^+$ form is ready for use.

The adsorption material according to the invention is very suitable for use in a method of separating hydrocarbon mixtures into saturated hydrocarbons and olefins, in which the mixture to be separated is passed in the gaseous state (e.g., the effluent of a gas chromatography injection system or pre-column) through an olefin trap filled with the adsorption material according to the invention. The saturated hydrocarbons (paraffins and naphthenes) pass through the column, while the olefins are retained in the column by adsorption on the packing material.

By increasing the temperature, the olefins can subsequently be desorbed. The desorption can be carried out in the reverse direction (back flush), with the olefins being obtained as a group, or in the forward direction (forward flush), which yields the olefins in the order of the number of carbon atoms.

The effluent from the olefin trap can subsequently be subjected to known per se gas chromatography separation techniques.

The adsorption material according to the invention is not only suitable for use in gas-solid chromatography, but can also be used for gas-liquid chromatography after being coated, in a manner known per se, with, for example, liquid polymers, silicones, and the like.

The invention is illustrated in and by the following example.

EXAMPLE

Preparation of the adsorption material 3 g Lewatit ® Sp-1080 (Merck), having a particle size of 0.10–0.25 mm, a porosity of 25%, an average pore diameter of 40 nm, an internal area of 25 m$^2$/g and 8% cross-linking were washed with 75 ml isopropanol to remove any organic materials. The polarity of the solvent was gradually increased by using water/isopropanol mixtures (20:80; 40:60; 60:40; 80:20; 4×25 ml). Subsequently, 150 ml deionized water was used to elute the column. The moist Lewatit column was then eluted dropwise with 100 ml of a 0.2 N silver nitrate solution in deionized water. The column was washed with 40 ml water, whereafter no elution of Ag$^+$ was observed (checked by means of a sodium chloride solution). The column was subsequently washed with 25 ml of a 1:1 water/isopropanol mixture. The material was poured into a cup and dried in a furnace at 50° C.

Using standard procedures, the olefin adsorption material was introduced into a gas chromatography column (1 m×2 mm). The column was connected in known manner in a gas chromatograph between an injector and a detector.

Chromatographic tests

A mixture consisting of 0.5% n-dodecane and 0.2% hexene-1 in n-octane, was passed through the column in the gaseous state. In spite of the much lower boiling point of hexene-1 (boiling point 63° C.), it was found that this compound was eluted from the column after the n-dodecane (boiling point 216° C.), which confirms the selective olefin retardation by the adsorption material according to this invention.

The principle of selective olefin retardation was confirmed further by experiments in which complex mixtures of hydrocarbons, such as a naphtha, were passed through the column.

In another experiment, a column of 0.25 m×2 mm was used as an olefin trap. The complex mixture to be separated was passed through the column at a temperature of 100° C. The olefins (hexene, cyclohexene, heptene, methylcyclohexene, octene, nonene and decene) were retarded. After undecane had been eluted from the column, the direction of flow was reversed and the temperature of the column was increased to 150° C. During this procedure the olefins came from the column and were detected as one peak, which demonstrated the suitability of the adsorption material as a group retarder. The desorbed olefins were subsequently, after hydrogenation, subjected to conventional gas chromatographic analysis, which yielded quantitative data about the various olefins present in the starting material.

The reversibility of the olefin adsorption by the adsorption material according to this invention was shown by analyzing a quantitative sample and comparing the proportions calculated on the ground of findings with the theoretical proportions. The results listed in the following table show that no olefins were lost during trapping and thermal desorption.

TABLE

|         | calculated (%) | theory (%) |
|---------|----------------|------------|
| heptene | 1.15           | 1.20       |
| octene  | 2.38           | 2.40       |
| nonene  | 1.58           | 1.60       |

It is seen, therefore, that the adsorption material according to the invention functioned as a reversible selective olefin trap and was very suitable for use as a packing material for a gas chromatography column.

Further experiments showed that best results were obtained when small particles in the order of 0.10–0.13 mm were used.

What we claim:

1. An adsorption material for olefins, comprising a thermostable resin containing strongly acid ion exchange groups to which $Ag^+$ ions are linked, characterized in that the resin is a macroporous resin with an average pore diameter of 10–100 nm, an internal area of 10–100 $m^2/g$ and 5–15% cross-linking.

2. An adsorption material as claimed in claim 1, characterized in that the strongly acid ion exchange groups are sulfonic acid groups.

3. An adsorption material as claimed in claim 1, characterized in that the resin is a polystyrene cross-linked with divinylbenzene.

4. An adsorption material as claimed in claim 1, characterized in that the particles have sizes in the range of 0.037–0.84 mm.

5. An adsorption material as claimed in claim 1, characterized in that the resin has a porosity of about 25%.

6. An adsorption material as claimed in claim 1, characterized in that the resin has a pore diameter of 30–100 nm.

7. An adsorption material as claimed in claim 1, characterized in that the resin has an internal area of about 25 $m^2/g$.

8. An adsorption material as claimed in claim 1, characterized in that the resin has approximately 8% cross-linking.

9. A gas chromatography column filled with an adsorption material for olefins as defined in claims 1, 2, 3, 4, 5, 6, 7, or 8.

10. An adsorption material as claimed in claim 1, characterized in that the resin has a pore diameter of about 40 nm.

11. A method of selectively removing olefins from a mixture of hydrocarbons comprising olefins and saturated hydrocarbons, in which the mixture to be separated is passed through a column containing an adsorption material for olefins comprising a thermostable resin with strongly acid ion exchange groups to which $Ag^+$ ions are linked, characterized by removing a group of olefins of different carbon numbers selectively and reversibly from a gaseous complex mixture of hydrocarbons comprising olefins and saturated hydrocarbons of different carbon numbers by gas chromatography, by using a gas chromatography column containing a macroporous, thermostable resin having strongly acid ion exchange groups to which $Ag^+$ ions are linked as an olefin adsorption material, which macroporous resin has an average pore diameter of 10–100 nm, an internal area of 10–100 $m^2/g$ and 5–15% cross-linking.

12. A method as claimed in claim 11, characterized in that the strongly acid ion exchange groups are sulfonic acid groups.

13. A method as claimed in claim 11, characterized in that the resin is a polystyrene cross-linked with divinylbenzene.

14. A method as claimed in claim 11, characterized in that the particles have sizes in the range of 0.037–0.84 mm.

15. A method as claimed in claim 11, characterized in that the resin has a porosity of about 25%.

16. A method as claimed in claim 11, characterized in that the resin has a pore diameter of 30–100 nm.

17. A method as claimed in claim 11, characterized in that the resin has an internal area of about 25 $m^2/g$.

18. A method as claimed in claim 11, characterized in that the resin has about 8% cross-linking.

19. A method as claimed in claim 11, characterized by selectively removing the olefins from a hydrocarbon mixture containing olefins and paraffins having 5–11 carbon atoms.

20. A method as claimed in claim 11, characterized by absorbing the olefins at a temperature of about 100° C. and a pressure of from about 100 to about 400 kPa.

21. A method as claimed in claim 11, characterized by desorbing the adsorbed olefins by raising the temperature to about 150° C.

22. A method as claimed in claim 21, characterized by desorbing the adsorbed olefins in the reverse direction and discharging them from the column as a group.

23. A method as claimed in claim 11, characterized in that the resin has a pore diameter of about 40 nm.

* * * * *